(12) United States Patent
Davis et al.

(10) Patent No.: US 8,781,214 B2
(45) Date of Patent: Jul. 15, 2014

(54) ENHANCED IMAGING FOR OPTICAL COHERENCE TOMOGRAPHY

(75) Inventors: John Davis, San Jose, CA (US); Ben Jang, Cupertino, CA (US)

(73) Assignee: Optovue, Inc., Fremont, CA (US)

( * ) Notice: Subject to any disclaimer, the term of this patent is extended or adjusted under 35 U.S.C. 154(b) by 698 days.

(21) Appl. No.: 12/909,648

(22) Filed: Oct. 21, 2010

(65) Prior Publication Data

US 2011/0103658 A1  May 5, 2011

Related U.S. Application Data

(60) Provisional application No. 61/256,277, filed on Oct. 29, 2009.

(51) Int. Cl.
*G06K 9/00* (2006.01)
(52) U.S. Cl.
USPC .......................................... 382/154; 382/128
(58) Field of Classification Search
USPC .................................................. 382/154, 128
See application file for complete search history.

(56) References Cited

U.S. PATENT DOCUMENTS

| | | | |
|---|---|---|---|
| 5,189,369 A * | 2/1993 | Takane et al. ................ | 324/306 |
| 5,412,763 A * | 5/1995 | Knoplioch et al. .......... | 345/424 |
| 5,923,789 A * | 7/1999 | Avinash ....................... | 382/276 |
| 6,912,293 B1 * | 6/2005 | Korobkin ..................... | 382/100 |
| 7,301,644 B2 | 11/2007 | Knighton et al. | |
| 7,480,058 B2 | 1/2009 | Zhao et al. | |
| 7,505,142 B2 | 3/2009 | Knighton et al. | |
| 7,744,221 B2 | 6/2010 | Wei et al. | |
| 8,165,377 B2 * | 4/2012 | Vaidya et al. ................. | 382/131 |
| 8,391,590 B2 * | 3/2013 | Yalla et al. ................... | 382/154 |
| 2002/0081009 A1 * | 6/2002 | Licato et al. .................. | 382/131 |
| 2003/0210814 A1 * | 11/2003 | Nelson ......................... | 382/131 |
| 2004/0086175 A1 * | 5/2004 | Parker et al. ................. | 382/154 |
| 2004/0126007 A1 * | 7/2004 | Ziel et al. ..................... | 382/154 |
| 2004/0175025 A1 * | 9/2004 | Knoplioch et al. .......... | 382/132 |
| 2005/0226482 A1 * | 10/2005 | Kuduvalli .................... | 382/128 |
| 2006/0126920 A1 * | 6/2006 | Rust .............................. | 382/154 |
| 2007/0003131 A1 * | 1/2007 | Kaufman ...................... | 382/154 |
| 2007/0008318 A1 * | 1/2007 | Matsumoto .................. | 345/424 |
| 2007/0046966 A1 * | 3/2007 | Mussack et al. ............. | 358/1.13 |
| 2007/0053553 A1 * | 3/2007 | Gerritsen et al. ............ | 382/128 |
| 2007/0115481 A1 * | 5/2007 | Toth et al. .................... | 356/511 |
| 2007/0172105 A1 * | 7/2007 | Bahlmann et al. ........... | 382/131 |
| 2007/0291277 A1 * | 12/2007 | Everett et al. ................ | 356/497 |
| 2008/0187204 A1 * | 8/2008 | Reeves et al. ................ | 382/131 |
| 2008/0297509 A1 * | 12/2008 | Matsumoto .................. | 345/424 |

(Continued)

OTHER PUBLICATIONS

International Search Report for related PCT Application No. PCT/US2010/53603, date of mailing Dec. 23, 2010.
International Preliminary Report on Patentability mailed May 10, 2012, in related International Application No. PCT/US2010/53603.
T. Bajraszewski et al., "Three-dimensional in vivo imaging by spectral OCT", Proc. SPIE 5316, pp. 226-232, 2004.

(Continued)

*Primary Examiner* — Kathleen Y Dulaney
(74) *Attorney, Agent, or Firm* — Haynes and Boone, LLP

(57) ABSTRACT

An imaging device to obtain images, comprising: an optical source; an x-y scanner receiving light from the optical source and directing it onto a sample; a detector receiving reflected light from the scanner; and a computer receiving a signal from the detector and providing a 3D data set containing voxels with a given voxel resolution of a sample, the computer further executing instructions for finding values other than a single axes sum to represent a set of voxels; composing a 2D image using the values.

20 Claims, 18 Drawing Sheets

(56) References Cited

U.S. PATENT DOCUMENTS

| | | | |
|---|---|---|---|
| 2009/0112094 A1* | 4/2009 | Qin et al. | 600/447 |
| 2009/0251140 A1* | 10/2009 | Bhardwaj et al. | 324/307 |
| 2010/0008557 A1* | 1/2010 | Matsumoto | 382/131 |
| 2010/0135558 A1* | 6/2010 | Ruth et al. | 382/131 |
| 2010/0239140 A1* | 9/2010 | Ruijters et al. | 382/130 |
| 2010/0266190 A1* | 10/2010 | Zagorchev et al. | 382/132 |
| 2011/0011190 A1* | 1/2011 | Subramaniam | 73/866.5 |

OTHER PUBLICATIONS

M. Wojtkowski et al., "Real-time and static in vivo ophthalmic imaging by Spectral Optical Coherence Tomography", Proc. SPIE 5314, pp. 126-131, 2004.

C.K. Hitzenberger et al., "Three-dimensional imaging of the human retina by high-speed optical coherence tomography", Optics Express, vol. 11, No. 21, pp. 2753-2761, Oct. 20, 2003.

* cited by examiner

Zig Zag Summation

Wire Frame Cube Viewed from Above

Z Sum View        Perspective View 720     730

ENHANCED IMAGING FOR OPTICAL COHERENCE TOMOGRAPHY

RELATED APPLICATIONS

This application claims priority to provisional application 61/256,277, filed on Oct. 29, 2009, which is herein incorporated by reference in its entirety.

BACKGROUND

1. Field of the Invention

The embodiments described herein relate generally to methods and systems for collecting and processing images in optical coherence tomography.

2. Description of Related Art

Current trends in ophthalmology make extensive use of 3D imaging and image processing techniques. Such images may be utilized for diagnosing diseases such as glaucoma, and other medical conditions affecting the human eye. One of the challenges posed by the current technological advances in imaging techniques is the efficient and meaningful processing of the massive amounts of data collected at ever increasing imaging rates. Some approaches have been to convert a 3D data set into a manageable two-dimensional (2D) image that then can be analyzed. Traditionally, a technique that has been used for data reduction from a 3D data set into a 2D image is that of 2D 'En Face' image processing. (See for example, Bajraszewski et al., [Proc. SPIE 5316, 226-232 (2004)], Wojtkowski et al., [Proc. SPIE 5314, 126-131 (2004)], Hitzenberger et al., [Opt Express. October 20; 11 (21):2753-61 (2003)], U.S. Pat. No. 7,301,644, or U.S. Pat. No. 7,505,142). This technique includes the summing of the intensity signals in the 3D data set along one direction, preferentially the Z-direction hereby identified with the axial direction of an Optical Coherence Tomography (OCT) scan, between two retinal tissue layers. The summation takes place among voxels having the same XY position. Typically, voxels located outside of the layers of interest are ignored during processing.

One common problem with this type of 'En Face' image processing technique and other volume rendering techniques is the appearance of artifacts created by the involuntary motion of the subject's eye while a data set is being collected. The movement introduces relative displacements of the collected images, so that physical features end up appearing discontinuous in the resulting 3D data set, rendering the entire set unreliable.

Another challenge that commonly occurs in such image processing is that of correlating a sequence of 3D data sets from a given sample, the different data sets having been collected during different imaging sessions spanning a long period of time. The sample can be a subject's eye, a selected vascular structure, or other selected region of interest. In this case, the lack of an efficient and reliable method for correlating each 3D data set to the same physical feature in the sample prevents an accurate assessment of the evolution of the images over time. In ophthalmology, for instance, such a change can be utilized to evaluate certain diseases or conditions in the subject.

What is needed is a better image processing technique that is capable of producing accurate and meaningful information.

SUMMARY

An imaging device to obtain images, comprising: an optical source; an x-y scanner receiving light from the optical source and directing it onto a sample; a detector receiving reflected light from the scanner; and a computer receiving a signal from the detector and providing a 3D data set containing voxels with a given voxel resolution of a sample, the computer further executing instructions for finding values other than a single axes sum to represent a set of voxels; and composing a 2D image using the values.

A method for enhancing ophthalmology images according to some embodiments of the present invention includes obtaining a 3D image data set containing voxels with a given voxel resolution of a sample; finding values other than a single axes sum to represent a set of voxels; and composing a 2D image using the values.

BRIEF DESCRIPTION OF THE DRAWINGS

FIG. 3b is an exemplary flowchart according to some embodiments described in FIG. 3a.

FIG. 4b is an exemplary flowchart according to some embodiments described in FIG. 4a.

FIG. 5b is an exemplary flowchart according to some embodiments described in FIG. 5a.

FIG. 10 shows examples of 2D images according to some embodiments described in FIG. 5a.

FIG. 11 shows examples of 2D images according to some embodiments described in FIG. 5a.

DETAILED DESCRIPTION

Existing imaging technology in ophthalmology makes extensive use of information-rich content in three-dimensional (3D) data sets obtained by imaging techniques such as optical coherence tomography (OCT). Particularly useful for the diagnostics and treatment of common diseases in ophthalmology are scanning techniques that provide images of the fundus of the eye, which is the interior surface of the eye, including the retina, optic disc, macula and fovea, and blood vessels spreading through the tissue. The retina is a light sensitive, layered tissue including an inner limiting membrane (ILM), a nerve fiber layer, a photo-receptor cell layer (also known as Inner Segment/Outer Segment (IS/OS)), including Rod and Cone cells, and a retinal pigment epithelium (RPE). A thorough clinical analysis of the retina includes a detailed and precise description of each of these layers. A problem that normally arises for imaging techniques is that the retina is a surface extending in two dimensions, with a thickness, and is curved and covers approximately 72% of a sphere of about 22 mm in diameter. This complex geometry calls for the use of methods and techniques for data processing that can provide accurate information about a subject's condition, and can be correlated through multiple images taken at different times. Another problem associated with imaging in ophthalmology is the involuntary motion of the subject's eye while a scan is being collected. This movement not only introduces blurring of the images, but may significantly destroy valuable information contained in a given data set if care is not taken to properly correlate physical features to their accurate position relative to other features in the collected data set.

Figure 12:
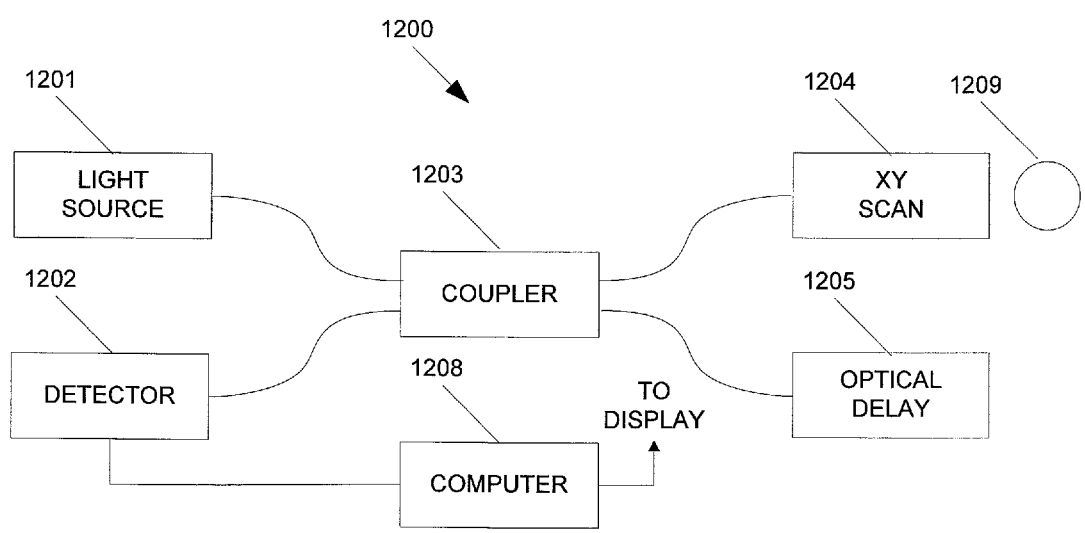
FIG. 12 illustrates an example of an OCT imager.

FIG. 12 illustrates an example of an OCT imager 1200 that can be utilized in enhancing an OCT data set according to some embodiments of the present invention. OCT imager 1200 includes light source 1201 supplying light to coupler 1203, which directs the light through the sampling arm to XY scan 1204 and through the reference arm to optical delay 1205. XY scan 1204 scans the light across eye 1209 and collects the reflected light from eye 1209. Light reflected from eye 1209 is captured in XY scan 1204 and combined with light reflected from optical delay 1205 in coupler 1203 to generate an interference signal. The interference signal is coupled into detector 1202. OCT imager 1200 can be a time domain OCT imager, in which case depth (or A-scans) are obtained by scanning optical delay 1205, or a Fourier domain imager, in which case detector 1202 is a spectrometer that captures the interference signal as a function of wavelength. In either case, the OCT A-scans are captured by computer 1208. Collections of A-scans taken along an XY pattern are utilized in computer 1208 to generate 3-D OCT data sets. Computer 1208 can also be utilized to process the 3-D OCT data sets into 2-D images according to some embodiments of the present invention. Computer 1208 can be any device capable of processing data and may include any number of processors or microcontrollers with associated data storage such as memory or fixed storage media and supporting circuitry.

A single element in a 3D data set obtained by a given scanning technique usually corresponds to a value for the signal strength in a detector, also referred to as 'intensity'. This value is associated with a coordinate in 3D space, which is the location in the tissue sample from where the signal is being collected. In the case of OCT, the signal strength corresponds to the intensity of the light backscattered from the tissue sample. In some embodiments, the OCT signal is obtained through a first 2D scanning of illumination source 1201 on sample 1209, which may include the fundus of the eye, displacing the beam from one point to an adjacent point along a first line with XY scan 1204, and repeating this for a selected pattern of lines on a 2D surface. As shown in FIG. 12, the illumination source 1201 may include a broadband light source that produces a range of wavelengths. In some embodiments, illumination source 1201 can be a swept laser source with a narrow linewidth output being swept across a broad tuning range. At each point in the first 2D scanning, a one dimensional profile of the tissue along a third dimension referred to as an 'axial direction' is obtained by OCT interferometer 1200.

In some embodiments of an OCT technique, the 'axial' profile is obtained by correlating the 'depth' coordinate Z with the spectral interference pattern produced by OCT interferometer. Some embodiments may further make use of a Fourier domain technique, as described in U.S. Pat. No. 7,480,058, which is hereby incorporated by reference in its entirety. The combination of a first scan in 2D and the axial profile results in a 3D grid of data values, where each value and position location can form a 'voxel'. Therefore, a voxel is associated with the coordinate point in the sample that corresponds to a given X-Y position of the 2D scan of the beam, and a 'depth' coordinate Z, associated with the axial backscattering light intensity profile.

The sampling resolution of the imaging technique is given by the dimensions of a single voxel in the 3D data set collected as described above. This can normally be divided in a 2D sampling resolution corresponding to the first scan of a laser beam in the XY plane, and the axial sampling resolution corresponding to the Z-axis, normally associated with the number of voxels acquired per OCT axial profile.

Figure 1:
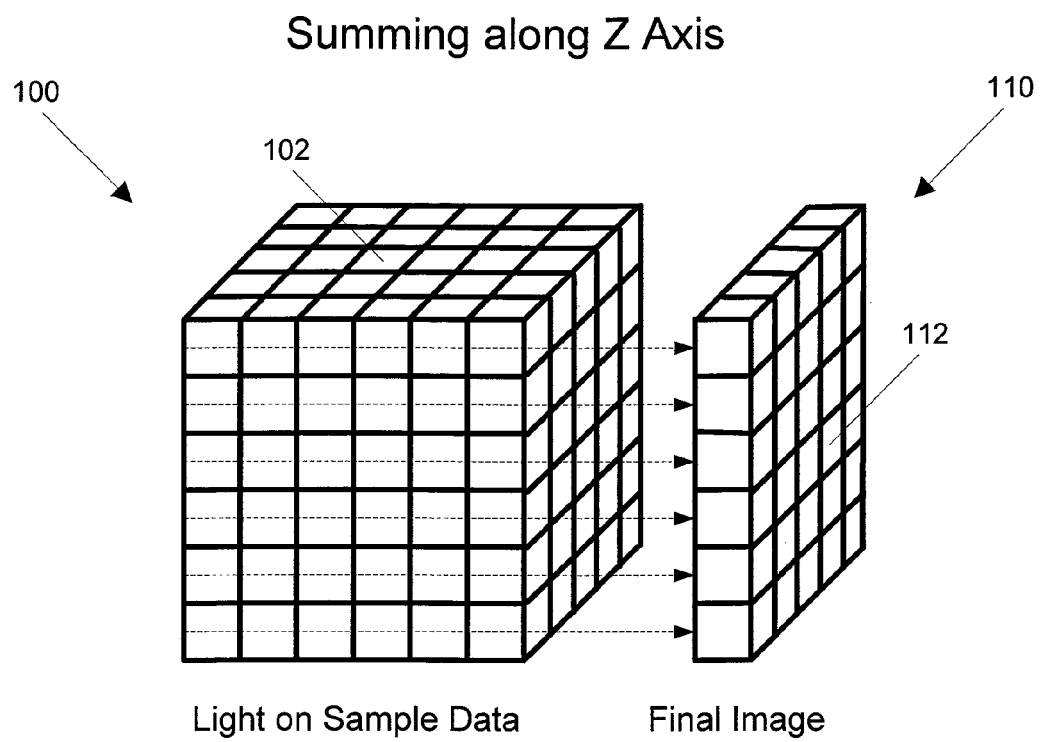
FIG. 1 shows an example of an 'En Face' image processing technique wherein the summing of the 3D data takes place along the Z-axis direction.
Figure 1:
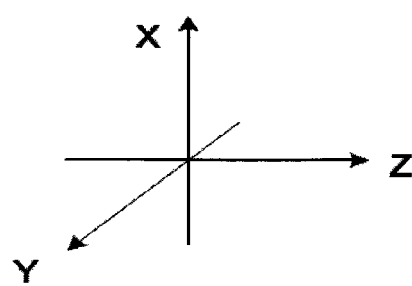

FIG. 1 shows an example of an 'En Face' image processing technique wherein voxels 102 of 3D voxel 100 are summed along a line in the Z-axis direction to yield a 2-D image 110. In other words, each pixel 112 of 2D image 110 is formed as the summation of voxels 102 that share the same X-Y coordinate. The result is a 2D image 110, with image pixel 112, that may be displayed using further brightness and contrast adjustments. (See for example, Bajraszewski et al., [Proc. SPIE 5316, 226-232 (2004)], Wojtkowski et al., [Proc. SPIE 5314, 126-131 (2004)], Hitzenberger et al., [Opt Express. October 20; 11 (21):2753-61 (2003)], U.S. Pat. No. 7,301,644, or U.S. Pat. No. 7,505,142).

The summing of voxels 102 can take place between two retinal tissue layers, and voxels 102 outside of the two layers can be ignored. All the voxels 102 considered in the summation have the same XY position. The sum of these voxel values 102 are then divided by the thickness between the two retinal layers.

Figure 2:
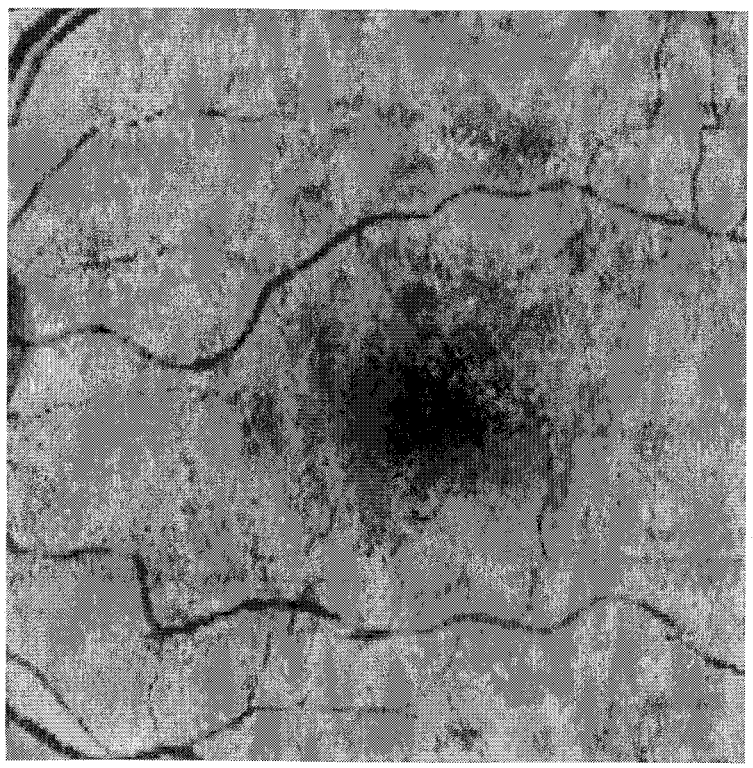
FIG. 2 shows an example image resulting from an 'En-Face' image processing procedure according to the method described in FIG. 1 above.

FIG. 2 shows an exemplary retinal image 200 created according to the 'En Face' technique described with respect to FIG. 1. The parallel projection view thus obtained in retinal image 200 lacks the natural perspective that one who is looking directly at the retina would normally have. In particular, the 3D shape of the retina is lost in image 200, and underlying lumps and other physical features will not be displayed in such a 2D image. Because the voxel data 100 has been summed, neither cross section nor thickness of the retinal layer may be displayed. Furthermore, the voxel summation along the axial direction may result in an inaccurate depiction of the position of each of the features relative to each other in the 2D 'En Face' image 200 in cases where the eye movement took place between or during two OCT line scans.

Figure 3A:
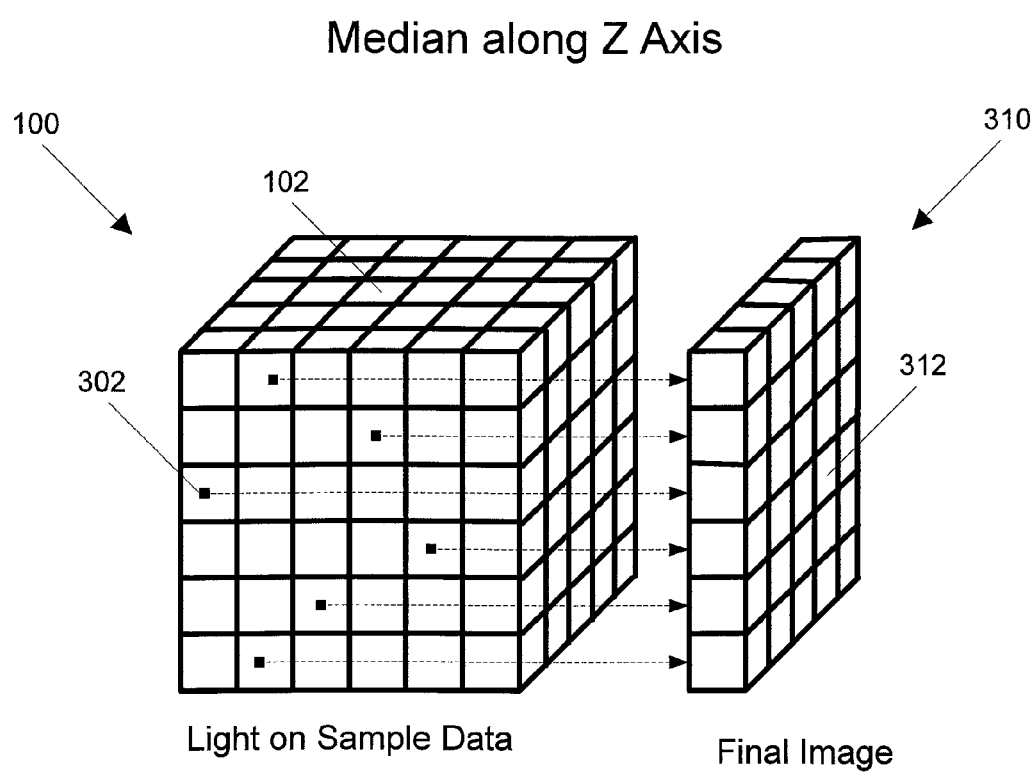
FIG. 3a shows an embodiment of the present invention wherein a 2-D image is formed from median values of voxels along the Z-axis.

FIG. 3a shows an embodiment of the present invention wherein the median value of the voxels 100 along the Z-axis is used to form each XY pixel 312 in the resulting 2D image 310. To obtain an image according to some embodiments as depicted in FIG. 3a, instead of summing voxels 102 along the Z-axis from the selected tissue layer, a single value 302 can be calculated from that same array of voxels 100 having a common XY position. At each XY location 312 of the resulting 2D image 310, the pixel calculated would have the median value for that Z column of values within the 3D data set 100. The resulting 2D image 310 may have less 'noise' than that described in FIG. 1 when voxels 100 of different layers are summed together without accounting for possible displacement artifacts between the layers. Furthermore, both the anatomy and pathology of the selected layers are shown by this method. Here, the selected layers would be that portion of the 3D data set in between the two retinal tissue layers where the median value is being considered. If a certain anatomic feature or a pathologic feature is included in the selected layer, e.g. a blood vessel, or a portion of inflamed nerve tissue, the median value will reflect the presence of this feature more clearly, as compared to an average value that tends to merge this anatomic or pathologic feature with the background image. In addition, an advantage of a technique according to some embodiments of the present invention as depicted in FIG. 3*a* is that no integration or summation of the data voxels is necessary.

Figure 3B:
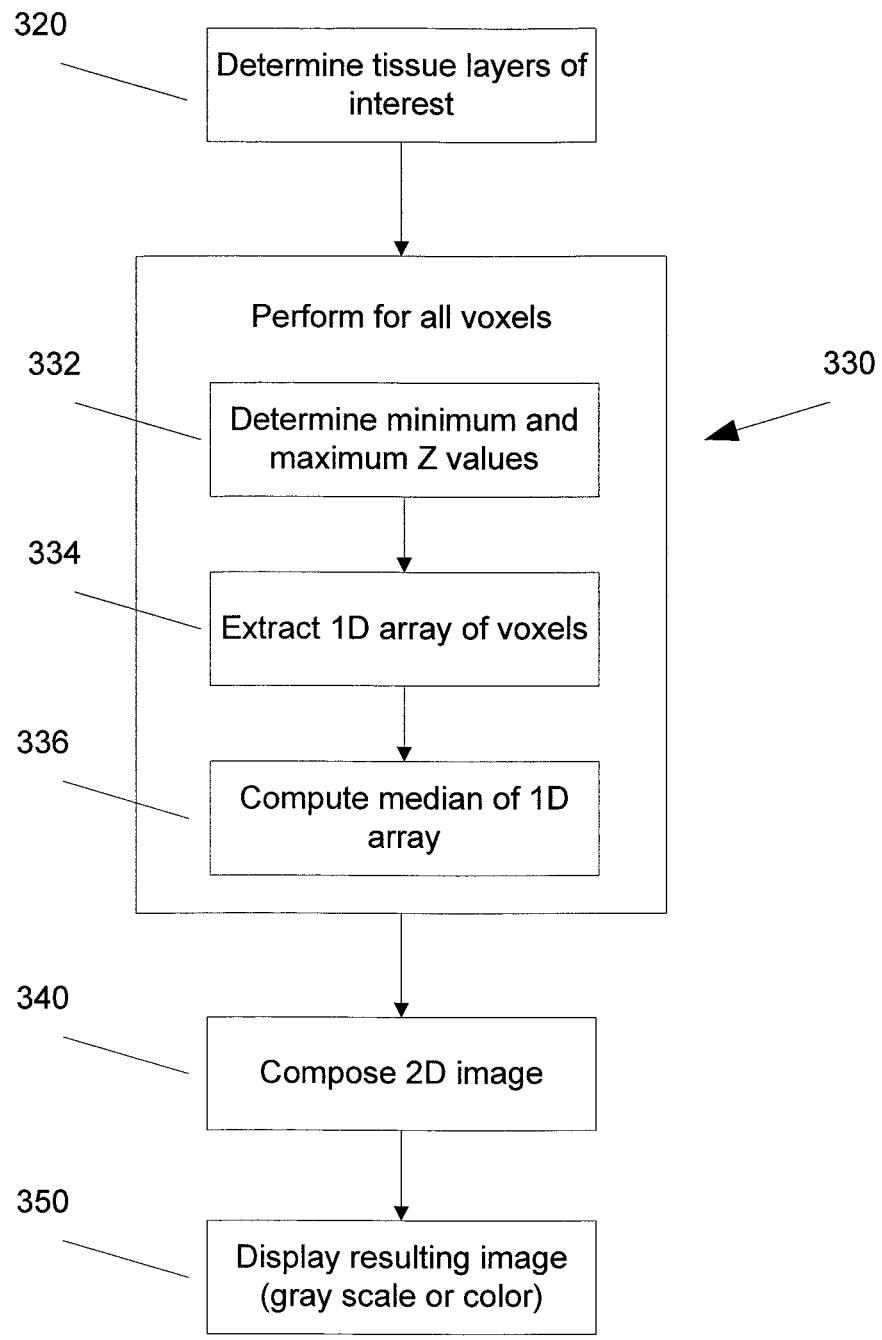

In detail, the technique depicted in FIG. 3*a* according to some embodiments of the present invention is further illustrated in FIG. 3*b*. As shown in FIG. 3*b*, tissue layers of interest are determined in step 320. In some embodiments, as shown in FIG. 3*a*, all voxels 102 are assumed to be of interest. However, in some embodiments only those voxels 102 that are between determined layers are of interest.

The voxels of interest are determined in step 320. In step 330, a median value of the pixels of interest is determined that corresponds with each of pixels 312. As shown in FIG. 3*b*, for each pixel 312, which may correspond to a particular X-Y location, a minimum and maximum Z value for voxels 102 that are of interest is determined. In step 334, a 1-D array of voxels, along the Z axis, is determined from the voxels 102 that are of interest. Then, in step 336 the median value of voxels 102 that are of interest is determined.

In step 340, 2D image 310 is composed by assigning the median value at each X-Y position to the corresponding pixel 312. In step 350, the image can be displayed either in gray scale or in color utilizing a look-up table to provide brightness and contrast adjustments.

Figure 4A:
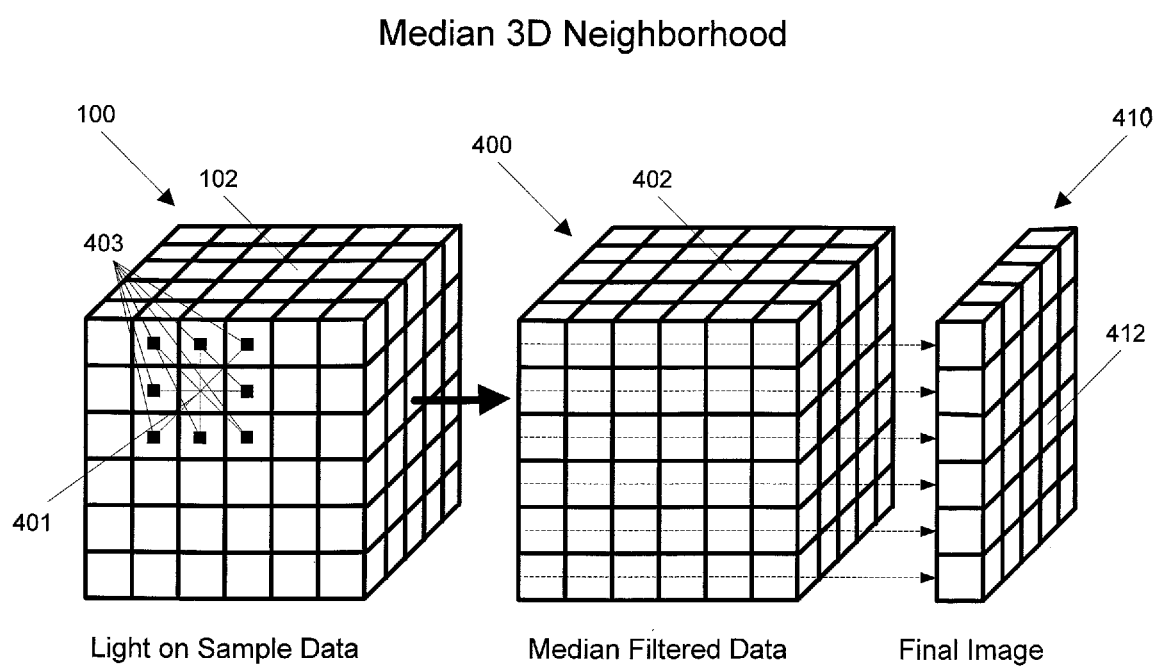
FIG. 4a shows an embodiment of the present invention wherein a 2-D image is formed by collecting the median from a 3D neighborhood for each voxel and summing the 3-D medians along the Z-axis.

FIG. 4*a* shows a method for image enhancement according to some embodiments of the present invention. In FIG. 4*a*, each voxel 102 of 3D data set 100 is replaced with a median voxel 402 of a 3D neighborhood of a given voxel 102 in a filtering step before further processing. For illustration, a 3D voxel 401 in data set 100 is first passed through a 3D median filter wherein a median value is associated with a given voxel according to the median obtained from a set of values selected from the vicinity 403 of the given voxel 401, including the given voxel 401 itself. The 3D data set 400 resulting from the 3D median filter and includes median values 402 is then processed to form the final 2D image.

In some embodiments of the present invention, further processing includes the summation of voxels 402 between two different layers of retinal tissue according to the XY coordinate of the voxels 400, as illustrated in FIG. 4*a*. With a 3D median filter, each voxel 401 in the data set is replaced with the median value 402 for the voxels 401, 403 in a selected 3D neighborhood around the voxel 401. For example, all the values in a 3×3×3 cube of voxels surrounding each voxel could be used to calculate an output median value. Neighborhoods having other sizes and shapes may be used, for example a 2×2×2 neighborhood or a 5×5×5 neighborhood may be used. Neighborhoods may have different dimension in every axis; for instance, a 3×1×3 neighborhood may be used. When a 3D median filter is used, the resulting value associated to a given voxel may actually come from a voxel with a different X, Y, or Z coordinate.

The 3D median filter technique in some embodiments as depicted in FIG. 4*a* may have the same advantages as some embodiments as depicted in FIG. 3*a*. For example, the resulting image 410 may have less 'noise' and the anatomy and pathology of the selected layer can be clearly shown. In addition, the use of a 3D median filter, in certain configurations, may be faster in computation time than a computation according to some embodiments depicted in FIGS. 3*a* and 3*b*, where the median is taken along the Z axis of the data set. This will be more noticeable in the case of thick tissue layers, where a larger number of voxels along the Z axis may imply a longer median computation time. Note also that in the 3D median filter technique, the integration or summation of results is not carried through using sample voxels 100 directly, but using the results of the 3D median filter 400 previously applied to the original 3D data set 100.

Referring to some embodiments of the invention depicted in FIG. 4*a*, there are several steps used to create this enhanced 2D image as depicted. In the example shown in FIG. 4*a*, image 410 has the same X and Y dimensions as the original 3D data set 100.

Figure 4B:
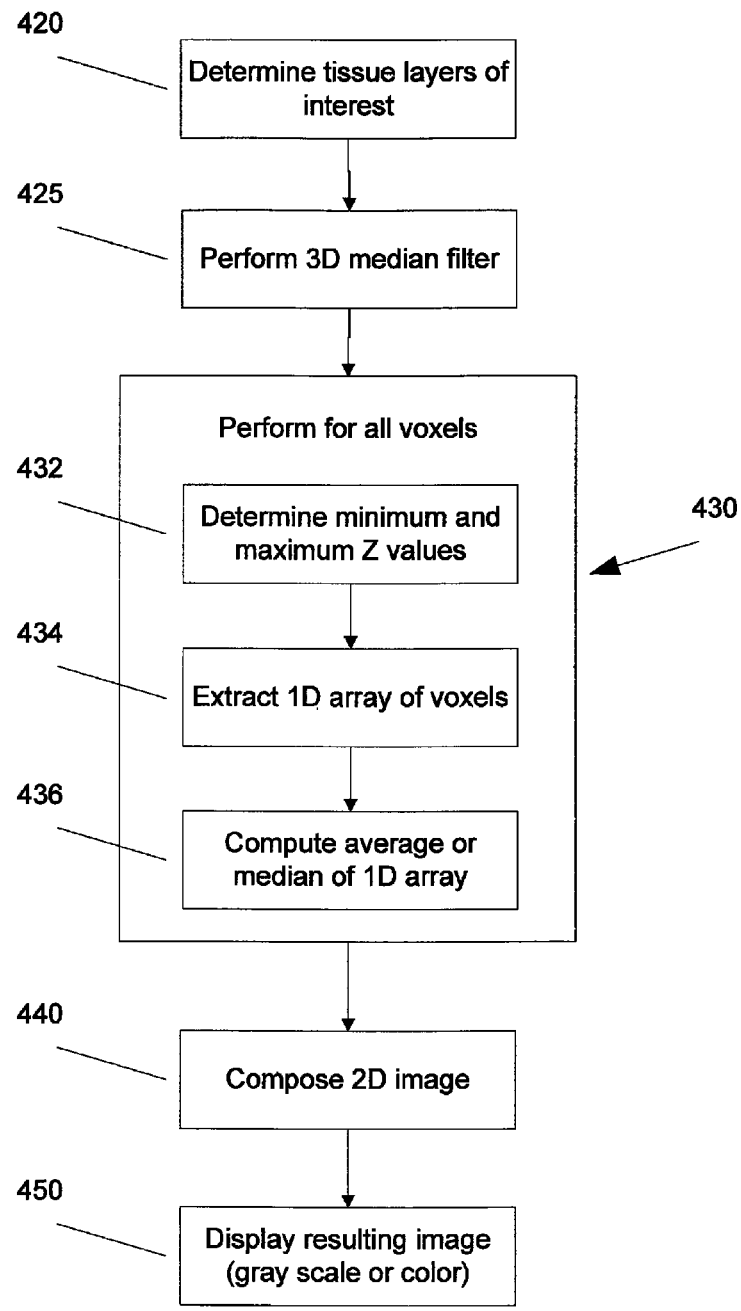

As shown in FIG. 4*b*, in step 420 voxels 102 of interest are determined. This is usually accomplished by determining those voxels 102 that lie between determined layers. FIG. 4*a* illustrates a particular example where all of voxels 102 are of interest. In step 425, a median filtering is performed. As described above, for each voxel 102 a median value 402 is determined utilizing the voxels in a particular 3-D volume around each voxel 102. Using median values 402 pixel 412 can be determined in step 430. In some embodiments, step 430 can be performed by first determining the minimum and maximum Z values corresponding to the X-Y location of pixel 412 to identify median values 402 that are of interest in step 432. In step 434, a 1D array of voxels having the current X,Y location and having an axial location ranging from the minimum to maximum Z values can be determined. In step 436, pixel value 412 can be determined by averaging, summing, determining the median, or otherwise processing the median values 402 that are of interest.

In step 440, the pixel value 412 is utilized to compose 2D image 410. 2D image 410 can then be displayed in step 450. 2D image 410 can be displayed with a gray scale or color lookup table to provide brightness and contrast adjustment.

Figure 5A:
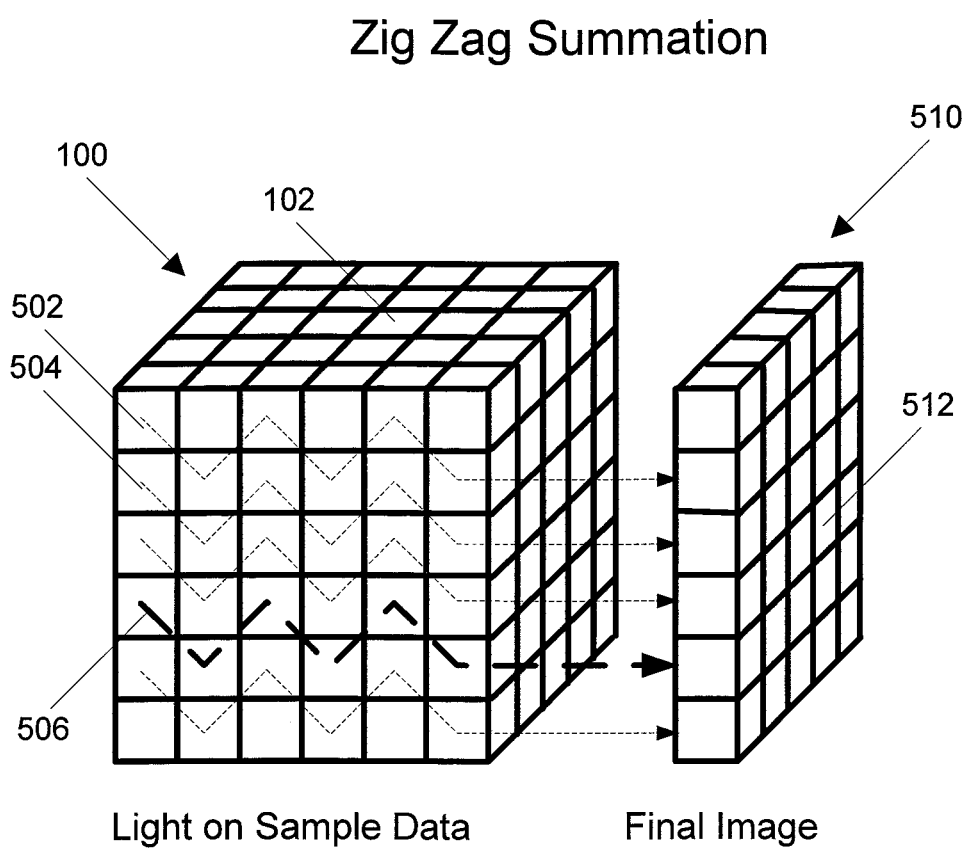
FIG. 5a shows an embodiment of the present invention wherein a 2-D image is formed by a 'zig zag' summation in the Z direction.

FIG. 5*a* shows a 'zig zag' summation method to produce a 2D image 510 from the 3D data set 100, according to some embodiments of the present invention. Instead of summing voxels directly along a line in the Z axis from the selected tissue layer, alternating voxels from adjacent Z columns 502 and 504 (for example, adjacent axial scans) are selected and then further processed, for example as summation, median, average, or other processing function. The path of summation (or other processing) can follow a zig zag pattern 506. The summation uses values from two or more axial scans 502 and 504 as opposed to other methods (as in FIG. 1) that use voxels from one axial scan for performing a summation at each X,Y output location. In some embodiments, one of the advantages of using values from more than one axial scan in the summation is to reduce the effects of scatter noise. Scatter noise tends to be canceled, or averaged out, between two axial scans located close to each other.

Figure 5B:
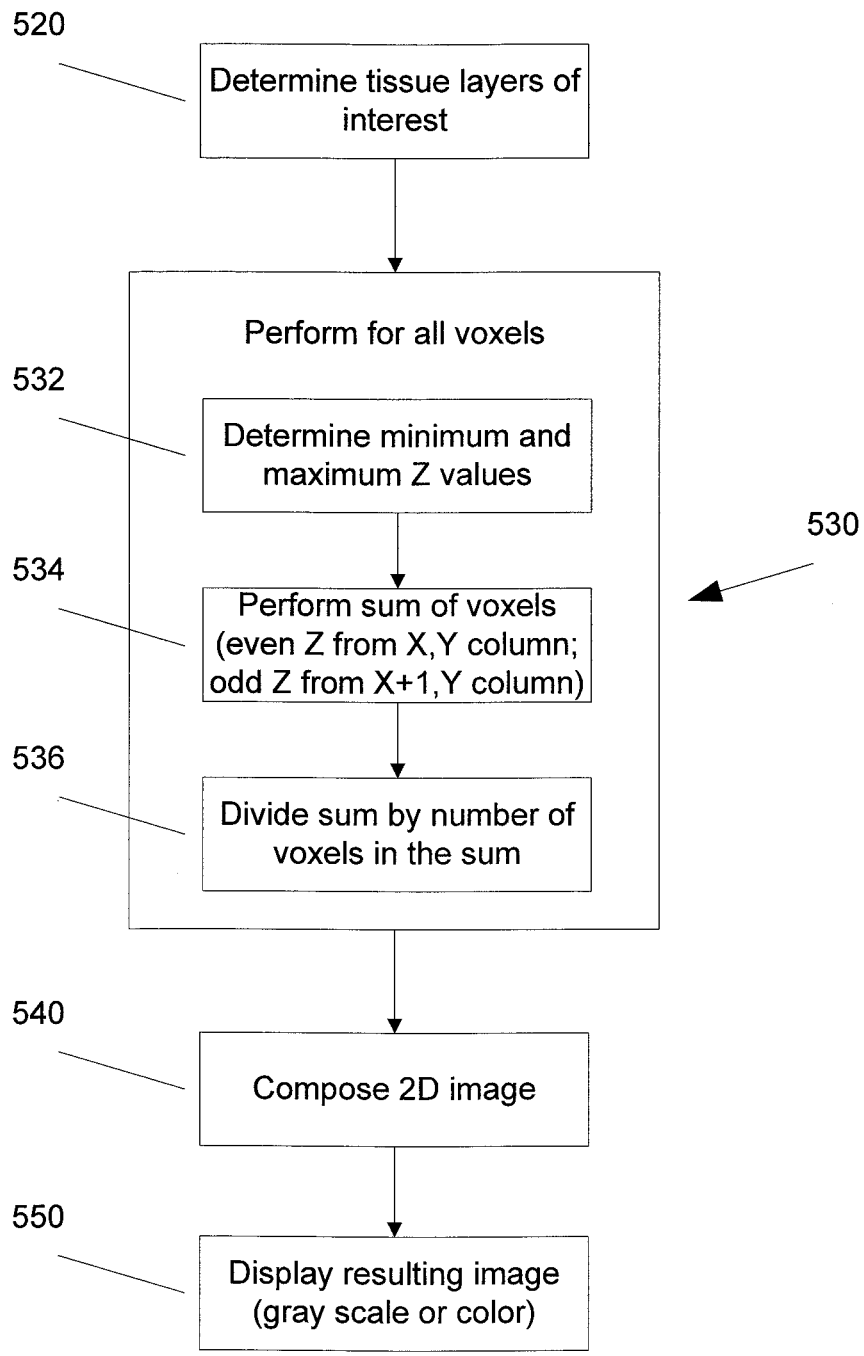

As noted in the previous embodiments, an image 510 with the same X and Y dimensions as the original 3D volume 100 is formed. As shown in FIG. 5*b*, in step 520 the tissue layers of interest are determined. FIG. 5*a* illustrates the case where all of voxels 102 in 3D image 100 are of interest. However, in some cases only voxels 102 that lie between determined layers are of interest.

In step 530, pixel values 512 are determined. As shown in FIG. 5b, for each of pixel values 512, in step 532 the minimum and maximum Z values that define voxels 102 that are of interest is determined. In some embodiments, from the 3D voxels 102, the sum of voxels from minimum to maximum Z such that voxels with an even valued Z come from the X,Y column 502 and voxels with an odd valued Z come from the (X+1), Y column 504. The summation for the last column uses (X−1), Y. In step 536, the sum is divided by the number of voxels 102 that are of interest in that direction to form an average. In step 540, 2D image 510 is formed utilizing pixel values 512 determined in step 530. In step 550, 2D image 510 can be displayed with a gray scale or color lookup table to provide brightness and contrast adjustment Furthermore, in some embodiments, other combinations may be chosen for process voxels 102 having an even/odd Z coordinate. As indicated above, processing may include summing, averaging, or taking a median. In some embodiments of the present invention, the voxel value may be squared before summation. In other embodiments, values having an even Z-coordinate may be chosen from the X, Y+1 column, and pixels having an odd Z-coordinate may be chosen from the X, Y column. Some embodiments of the present invention may use a 'helicoidal' combination of voxels along the axial direction, Z, which resembles a 'staircase' sum, or a 'screw' sum, whereby voxels having a Z-coordinate with a value of 0 modulo 4 (that is, the Z coordinate of the voxel is divisible by 4 with an integer residue of 0) are chosen from column X,Y; voxels having a Z mod 4 coordinate equal to 1 are chosen from column X+1, Y; voxels having a Z mod 4 coordinate equal to 2 are chosen from column X+1, Y+1; and voxels having a Z mod 4 coordinate equal to 3 are chosen from column X, Y+1. The above summation method uses values in different X and Y column in either a 'zig zag' or 'helicoidal' manner with a step size of one voxel. A different step size can be selected to cover the same depth with less computation time or selected based on the desired effect of different voxel sampling.

In some embodiments, using the 'zig zag' approach as described above is to reduce scatter noise inherent in OCT data by combining voxels from adjacent axial scans. As a result, anatomy and pathology of the selected tissue layers can be more clearly shown and the image details obtained are improved compared to techniques that average out over a larger set of voxel neighbors.

Figure 6A:
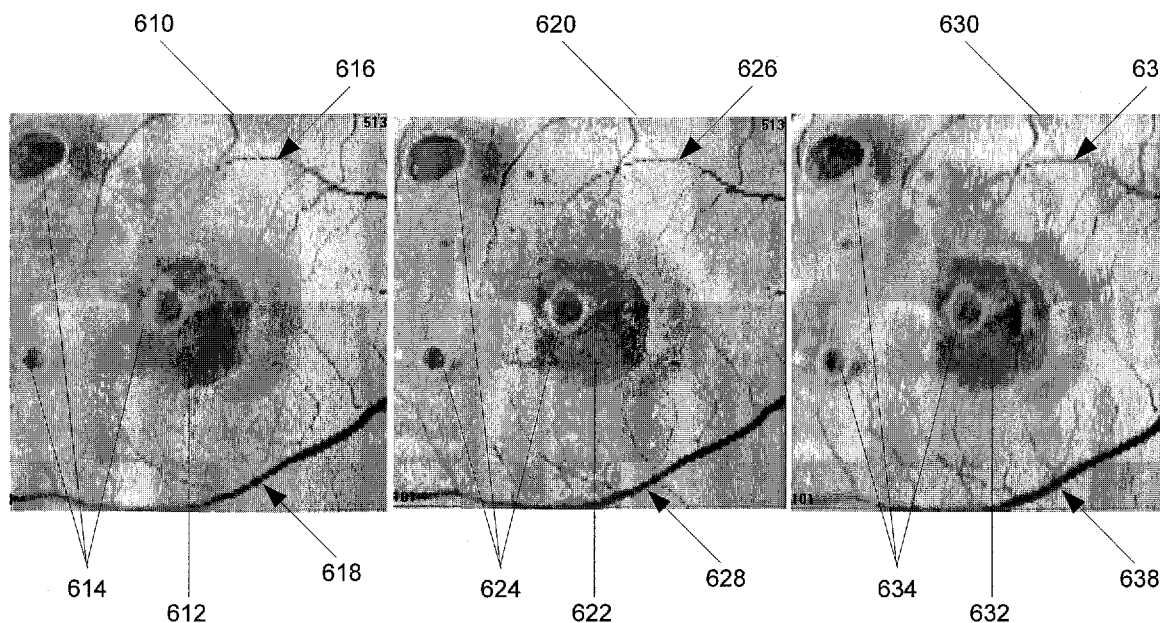
FIG. 6a shows 2D images of a segment of the RPE obtained from a 3D data set.
Figure 6B:
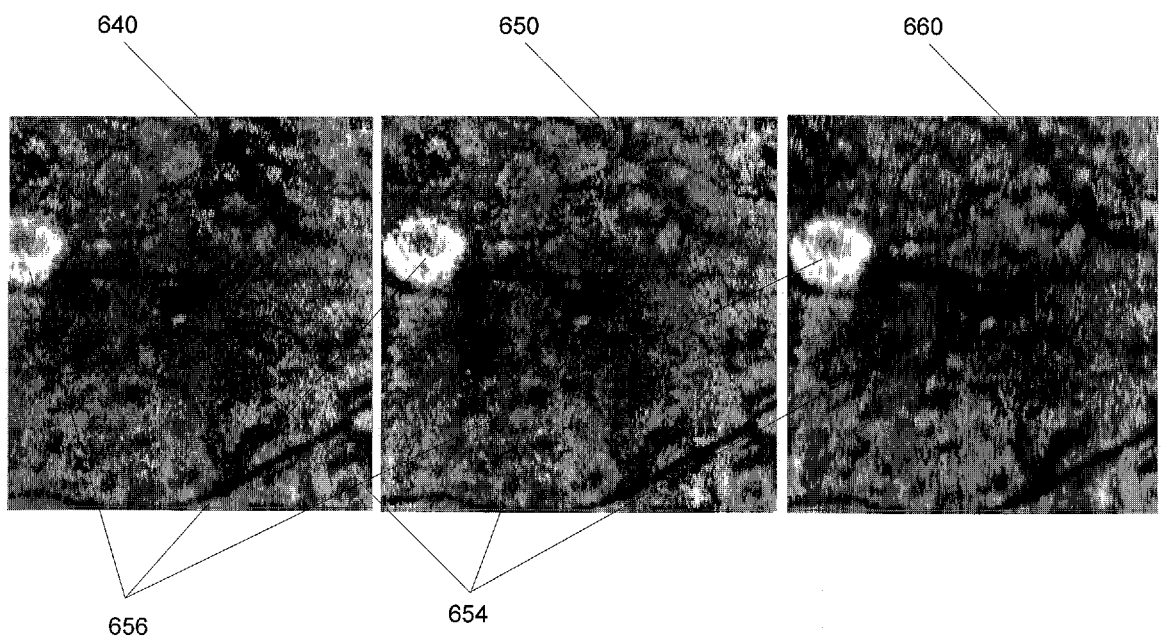
FIG. 6b shows 2D images of a segment of the RPE obtained from a 3D data set.
Figure 6C:
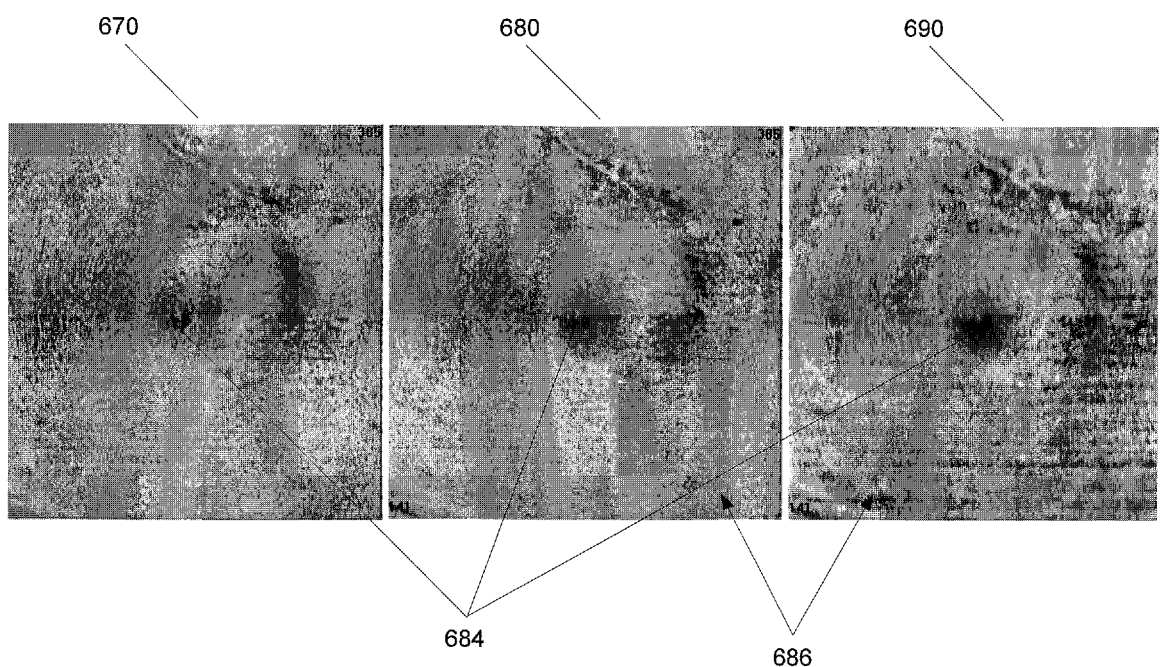
FIG. 6c shows 2D images of a segment of the ILM obtained from a 3D data set.

FIG. 6a illustrates the different results obtained when processing a 3D data set to produce a 2D image according to some embodiments of the present invention, as described above. The 3D data set corresponds to the retinal pigmented epithelium (RPE) from a single subject and was collected using an OCT raster scan of the region of interest, where light source 1201 is a white light illumination source. Axial information can be obtained by spectral decomposition of the OCT spectral interference signal from OCT system 1200, as described above. The images in FIG. 6a correspond to a tissue layer having a thickness equivalent to 60 μm in the Z direction, wherein all the voxels are considered in generating the final 2D images 610, 620, and 630. The tissue layer is offset by 60 μm into the axial direction relative to a reference surface (the RPE surface in this case) so that a selected portion of the RPE region of the retina can be analyzed. The reference surface used to generate the images in FIG. 6a is a geometric surface specifying the expected RPE boundary in a healthy eye. The images 610 to 660 in FIGS. 6a and 6b are generated from a 3D data set obtained using a scan pattern in a commercially available OCT imaging device. The images 670 to 690 in FIG. 6c are generated from a 3D data set 100 obtained using another scan pattern in the imaging device. For the example given in FIGS. 6a-c, voxel resolutions in the X, Y, and Z directions are 11.7 μm, 60.0 μm, and 3.0 μm, respectively. The pixel resolutions in the X and Y directions can be adjusted by using different scanning protocols to sample the same area to satisfy different needs. For instance, the voxel resolutions in the X, Y, and Z directions can employ a range from 5 μm to 40 μm, 40 μm to 80 μm, and 1 μm to 5 μm, respectively.

Some of the conspicuous features in FIG. 6a are the subretinal fluid regions that appear as dark discs 612, 622, and 632 in the centers of images 610, 620, and 630, respectively. Other dark spots 614, 624, and 634 surrounded by white rings at the center, center-left, and upper-left corner, respectively, represent the areas of persistent epithelial defects (PED), frequently seen for subjects having age-related macular degeneration (AMD). Also, the superior blood vessels 616, 626, and 636 and inferior blood vessels 618, 628, and 638 are clearly visible, crossing the entire field of view. The distribution and size information of the blood vessels provide critical information that may be useful for the diagnosis of diverse retinal diseases.

FIG. 6a illustrates an En Face image 610, a "zig-zag" image 620, and a median image 630. En Face image 610 is produced as discussed with FIG. 1. "Zig-zag image 620 is produced as illustrated in FIGS. 5a and 5b. Median image is produced as illustrated in FIGS. 4a and 4b. As shown in FIG. 6a, 'zig zag' summation image 620 has a reduced 'graininess' as compared to the result of the Z summation image 610 (or 'En Face' image). Also, median image 630, which utilizes a 2×2×2 neighborhood, shows a poorer resolution relative to image 620, but a smoother rendering of the physical features.

FIG. 6b shows 2D image renderings analogous to those shown in FIG. 6a, except that in FIG. 6b the 2D summation is collected over a span of 120 μm in the axial direction (Z-direction), with an offset of 120 μm relative to the outer surface of the retina. The 3D data set used in the rendering of the three 2D images 640, 650, and 660 is the same as in FIG. 6a, as can be seen from the patterns formed by the blood vessels. In this case it is clearly seen that a greater depth in the Z-direction gives the median image rendering 660 an advantage in terms of the contrast and smoothness of the features. Clearly, the graininess and noise accumulated with a direct Z summation severely reduce the quality of image 640. At the center of the three images 640, 650, and 660, the fovea 654 is still visible. The bright spot 656 that appears in 2D images 640, 650, and 660 is not an artifact from the 2D image calculation. Such bright spot 656 is a feature of the data set. It may be caused by a pathology in the upper tissue layers of the retina which allows more light to reach the lower tissue layers in the retina, whereas images 640, 650 and 660 show the lower tissue layers of the retina. Such pathology may be related to a choroidal defect, possibly caused by choroidal neovascularization.

FIG. 6c shows 2D image renderings analogous to that of FIGS. 6a-b, except that in the case of FIG. 6c the image is collected from data over a span of 30 μm in the axial direction, with zero offset relative to the outer surface of the retina. The tissue layer represented in 2D images 670, 680 and 690 is therefore the inner limiting membrane (ILM) of the retina (cf. above description). The contrast of the 2D rendered images clearly increases from direct Z summation image 670, to zig zag summation image 680, and median neighborhood sum image 690. Again, the fovea 684 is clearly discernible at the center of images 670, 680 and 690. Note that the horizontal direction of the raster scan 686 appears as left-right artifacts in the three images 670, 680 and 690; however, zig zag image 680 reduces this horizontal artifact relative to median image 690.

Additional 3D imaging processing techniques can help the visualization and understanding of the 3D data set to produce more accurate and meaningful information. Examples of such techniques are perspective image processing and volume rendering methods that can reveal information available in a 3D data set. These methods are described in details below.

Figure 7A:
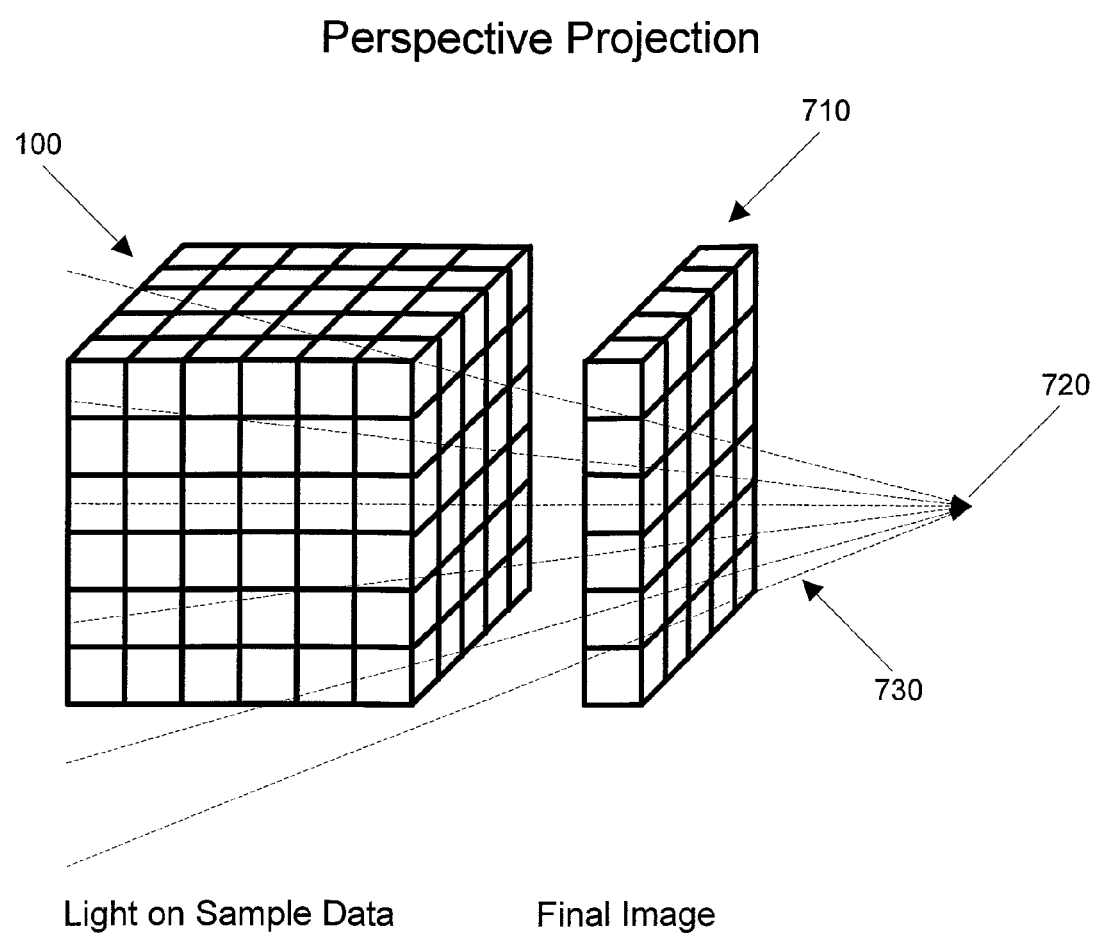
FIG. 7a shows a volume rendering process is used to create a 2D image using a perspective projection method according to some embodiments of the present invention.

FIG. 7a shows a perspective projection from a specific view point 720, and the summation method in a volume rendering technique according to some embodiments of the present invention. Volume rendering can of course be done from any other view point. However, even from the specific view point 720 shown in FIG. 7a, it is clear that the result of a summation of voxels along the 'light on sample data' directions 730 in FIG. 7a provides a different image 710 compared to the image resulting from voxel summation along the z-axis (cf. 110 in FIG. 1).

Figure 7B:
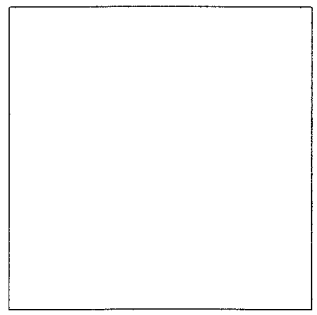
FIG. 7b shows an embodiment of the present invention wherein a volume rendering process is used to create exemplary 2D representations of 3D frame cubes.
Figure 7B:
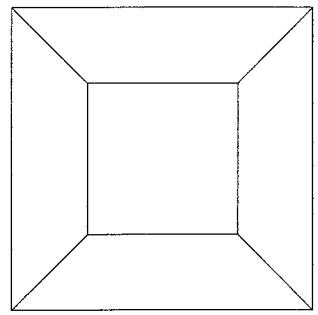

FIG. 7b illustrates the difference in a 2D image obtained between a summation along the Z-axis, as in FIG. 1, and a summation along the 'light on sample data' directions, according to some embodiments of the present invention depicted in FIG. 7a. FIG. 7b uses by example a wire frame cube viewed from the same view point 720 using the two methods. Further referring to FIGS. 7a and 7b, to emphasize the original data values (over the shape of the surface), shading can optionally be turned off to eliminate highlights from the light calculation, which might be distracting from some angles. Also, transparency can be adjusted so all selected voxels 100 contribute to the final image 710, not just the surface pixels. Finally, a color table (or grayscale, as shown herein) can be adjusted to provide brightness and contrast adjustments. The result can then be viewed from any angle and the image can be cropped to show tissue detail inside the layer.

Figure 8:
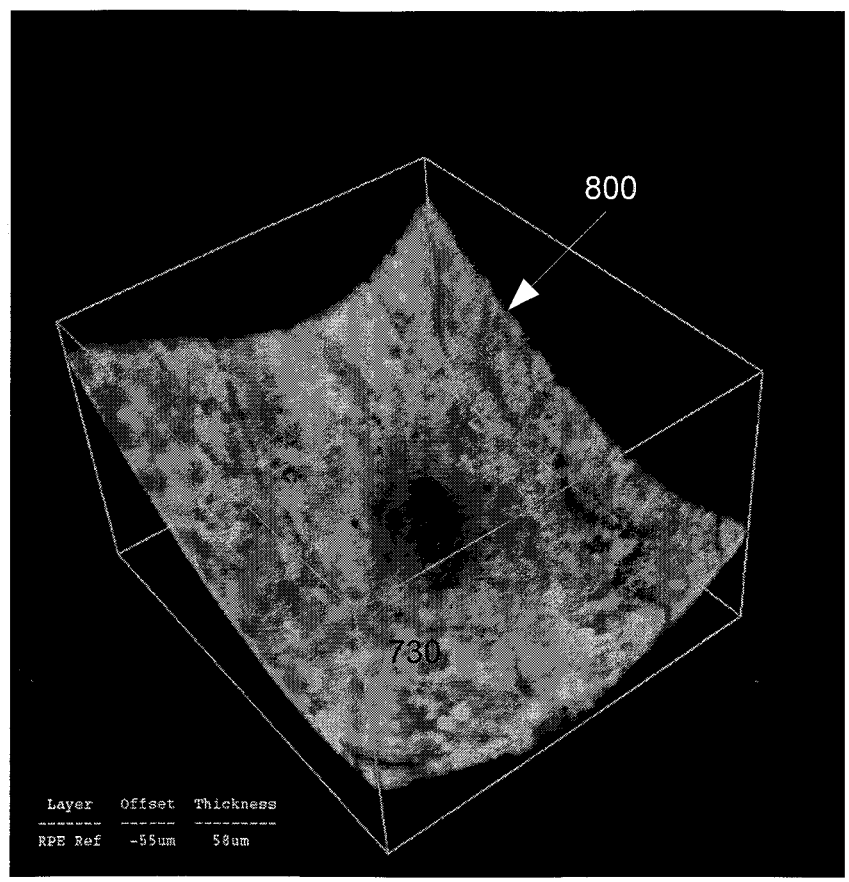
FIG. 8 shows an example result of using a volume rendering using a 3D mask according to some embodiments of the present invention.

FIG. 8 shows an example of a volume rendered image 800 collected from the same 3D data set 100 as the one used to generate image 200 in FIG. 2. FIG. 8 was obtained using a volume rendering alternative according to some embodiments of the present invention. This involves creating an anti-aliased mask based on retinal tissue layer anatomy. The mask could include tissue between two different layers and exclude all other tissue. Alternatively, the mask could take the surface of one layer and offset it to two different axial locations (in the direction of the Z-axis). The tissue between the two offsets would be included in the mask. The mask is used as an alpha channel of the volume during rendering to hide unwanted tissue in the 3D data set. An alpha channel controls the level of transparency of each voxel of a 3D data set or each pixel of an image. The alpha channel is used when compositing two or more data sets together to determine the contribution of each voxel to the final voxel at a given location.

It should also be noted that this 3D image 800 can include a depth buffer (in the direction of the Z-axis). If other geometric constructs are added to the 3D scene, this buffer is used during rendering to determine how those constructs intersect with the data set. For example, a vertical plane with original OCT data could be placed in the 3D scene to show where the layer is, vertically, by overlapping and correlating the 3D data set and the vertical plane including the OCT data. By comparison, images obtained through summation along the Z-axis, as in FIG. 1, provide no 3D information and so do not allow correlating data sets in this manner.

In some embodiments of the present invention, the 3D rendering shown in FIG. 8 can be created as follows: (a) Determine geometric location of tissue surface(s); (b) Use tissue surface to create a 3D mask; (c) Combine the 3D mask with original 3D data set; (d) Setup the rendering parameters; and (e) Render the image.

The details of how to determine the geometric location of tissue surface is complex. In general, the detection of layer surfaces can be performed by 1D intensity or texture profile analysis. Using the 1D intensity profile as an example, a 1D intensity profile at a location (X,Y) can be constructed by mapping all the intensity values along the Z-axis (axial scan or A-scan direction). To make the 1D intensity profile less sensitive to scattering noise, the 1D intensity profile at the location (X,Y) may be given by the average or median value around (X,Y) for each depth location Z. A 1D transition (edge) detection method can then be applied to find the rising and falling edges that define the layer of interest. Depending on the layer of interest, there are a few parameters involved in the detection such as search range, operating window size, and minimum edge strength threshold. Finally, a 2D surface smoothing method may be applied to smooth the layer surfaces at all (X,Y)s, to conform the anatomical information of the layer of interest.

The resulting 2D surface describes the geometric location of a tissue layer in 3D (like a curved sheet of paper). This can be used to create a 3D alpha mask for use during volume rendering. The mask will hide tissue above and below the tissues of interest. With proper transparency settings, this results in a 3D En Face image 800. To compute a mask, a top and a bottom surface are used. These two surface can come from:

2 different tissue surfaces (these surfaces could also be translated by Z offsets)

the same surface description translated by 2 different Z offsets 2 intermediate tissue surfaces computed by interpolating between known surfaces The mask is created by allocating a volume the same size as the original 3D data set and filling it with alpha (transparency) values. Voxels below the bottom surface and above the top surface are given fully transparent (e.g. zero) values. Voxels between the two surfaces are given opaque values (e.g. 255 for an 8 bit mask). Image quality can be improved by calculating intermediate transparency values along both surfaces to produce a smoother anti-aliased mask. The original 3D data set and the mask are then combined to form a single 2 component volume. The original 3D data set is the luminance channel, while the mask is the alpha channel. During rendering, the mask values are combined with a global transparency function, so that the overall transparency of the final 3D En Face image 800 can be adjusted.

Finally, the 3D En Face image can be rendered. Rendering of such image is performed by standard volume rendering software, for example, VTK from www.vtk.org can be used.

There are a number of benefits to this method. The method:
1. Provides a true perspective view of the 3D data set, not a warped parallel projection view;
2. Allows viewing of the data set from any angle, including from the top or bottom;
3. The final rendering shows the shape of the tissue layer, including lumps that may indicate pathology;
4. By cropping into the 3D data set, the internal structure of different layers can be displayed;
5. The thickness and other details of different layers can be shown; and
6. A 2D surface of pixels from the 3D OCT data set can be inserted and overlaid into the 3D data set to show where different layers are relative to one another. This surface can be interactively moved to show different locations in the data set. This surface can be a 2D plane containing all the pixels in one X-Z plane for one fixed Y value, for example.

When a 3D data set is constructed, the X, Y, and Z voxel dimensions determine the maximum degree of accuracy expected for an alignment of two consecutive 3D data sets from OCT scans. Unfortunately, unavoidable eye movement of a subject during image acquisition will generate misalignment between consecutive OCT scans. Furthermore, this effect will be increased due to the relative displacement of consecutive OCT data sets generally not in exact multiples of the voxel dimension in X, Y, and Z direction. Therefore, alignment with sub-voxel accuracy is desirable, especially when motion defects appear in the 2D 'En Face' image. Sub-voxel alignment of a 3D data set can be implemented in the following way.

First, the data size along each dimension is up-scaled by a factor of 'k'. Assuming that an original 3D data set contains a total of N voxels, this has the effect of creating a number of $(k^3-1) \times N$ new voxels with the same X, Y, and Z voxel dimensions as the original voxels, spaced in between the original voxels, where the new voxels are assigned specific intensity values. These intensity values can be determined by an interpolation technique, such as linear or cubic-spline interpolation. The 3D up-scaled data set is then aligned by an iterative process, until an optimal 3D alignment offset vector (i.e., $\Delta X$, $\Delta Y$, and $\Delta Z$) is achieved such that the resulting 2D 'En Face' image conforms well to anatomical physiologies. For example, blood vessels should be continuous in all dimensions. In some embodiments of the present invention, a multi-scale coarse-to-fine technique is used to accelerate the iterative alignment process. Finally, sub-voxel alignment in the original dimension can be achieved by dividing the optimal alignment offset vector by k. In some interpolation technique, the 'En Face' image f(X,Y) at the location (X,Y) may not only be contributed from the voxels of the same (X,Y) or a small local neighborhood, but also from those voxels of distant location; depending on the severity of the misalignment produced by the unavoidable eye movement of the subject's eye during a scan.

By introducing a sub-voxel positioning resolution as described above, defects in an image due to eye motion can be reduced below the ordinary voxel resolution of the system. This more robust alignment technique helps generate a 3D baseline data set of the subject's eye for further data registration and eye image correlation in subsequent imaging sessions, either within a single visit or across future visits for eye exams. Furthermore, having a more accurate 3D baseline data set improves subsequent image processing techniques, such as segmentation and enhancement, to be even more reliable; such may lead to better diagnosis.

Figure 9:
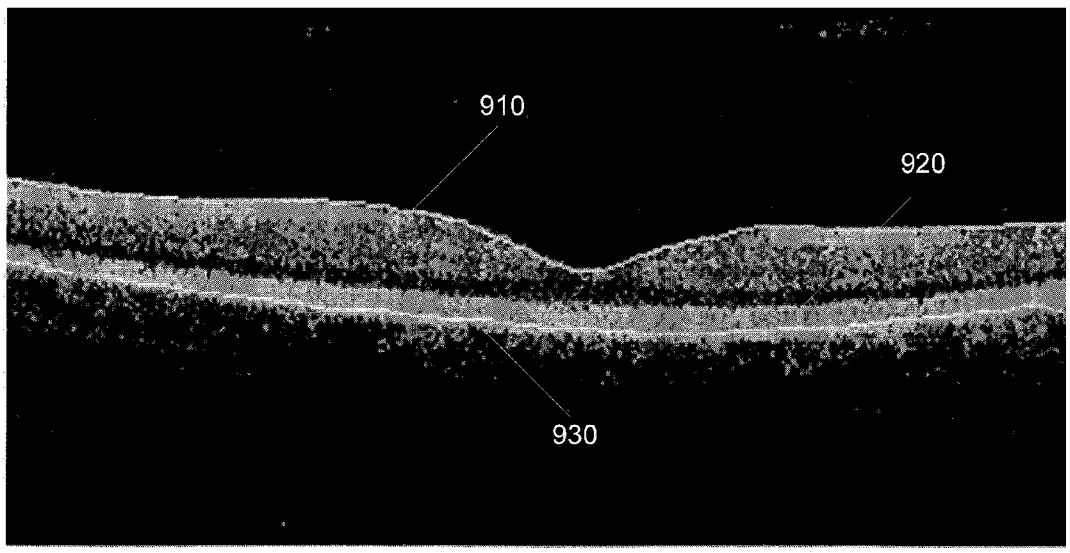
FIG. 9 shows an example of a 2D image in an XZ plane, obtained by an OCT imaging technique.

FIG. 9 shows an example of a typical 2D OCT image of the human retina and some of its associated feature curves; namely, Inner Limiting Membrane (ILM) 910, Inner/Outer Photoreceptor Segments (IS/OS) 920, and the Retinal Pigment Epithelium (RPE) 930. These feature curves are example segmentation improvement using the sub-voxel alignment technique outlined above.

Figure 10:
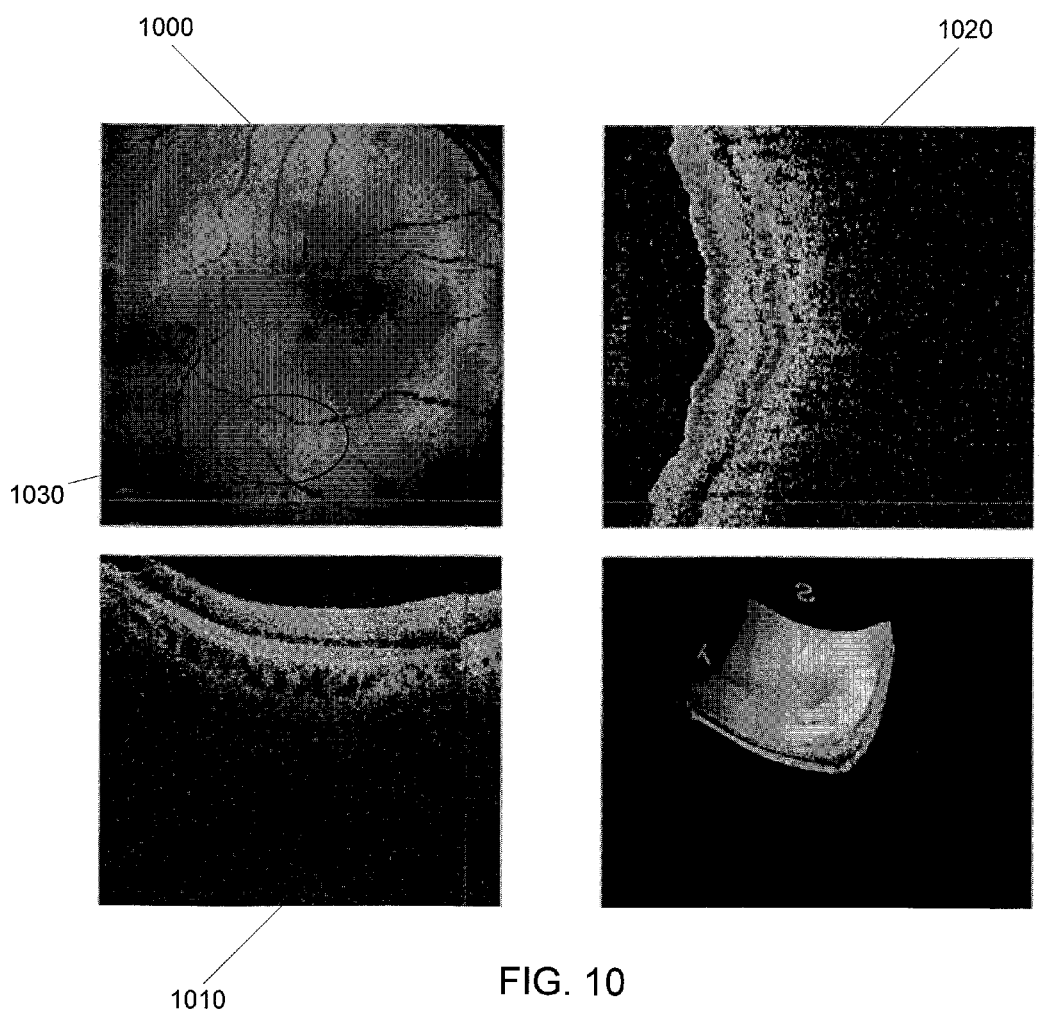
Figure 11:
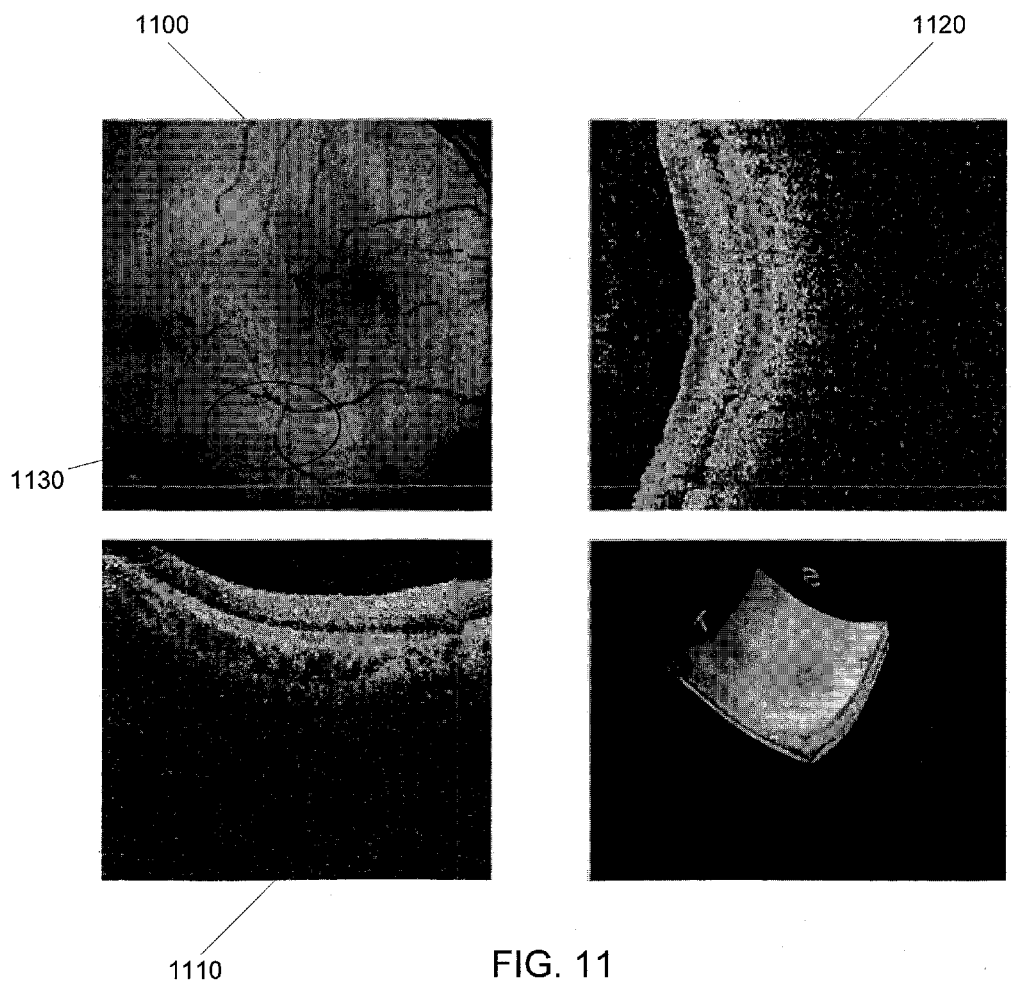

Due to computation efficiency and to facilitate alignment by region-of-interest, another 3D alignment technique is disclosed; the results of not performing this alternative alignment technique and those performing such techniques are shown in FIGS. 10 and 11, respectively. This 3D region-of-interest image alignment is also an iterative process in which a feature curve of a given 2D OCT scan image, for instance, RPE 930 in FIG. 9, is offset by a 3D vector ($\Delta X$, $\Delta Y$, and $\Delta Z$). According to some embodiments of the present invention, there is an offset vector for each of the multiple 2D OCT scans in a given 3D data set. FIGS. 10 and 11 show an example of a pair of 2D OCT scans along the XZ direction 1010 and 1110, and along the YZ direction 1020 and 1120. In other embodiments of the present invention, the 2D OCT scans can be along different directions. For example, a pattern of 2D OCT scans that includes a plurality of radial lines crossing at a center, and a plurality of concentric circular lines surrounding the optic disc, such that the center of the circular lines is the same as the crossing point of the plurality of radial lines, as described in U.S. Pat. No. 7,744,221, incorporated herein by reference in its entirety.

The search ranges of the alignment offset vectors can be pre-determined empirically based on anatomical physiologies or clinical needs. For each offset vector ($\Delta X$, $\Delta Y$, and $\Delta Z$), a 2D simulated scanning laser ophthalmoscope (SSLO) image, such as 1000 and 1100, is generated similar to a fundus image or an 'En Face' image, composed by incorporating all the tissue signals of the scanned OCT images and considering all voxels of interest according to some embodiments as described in FIGS. 5a and 5b. Landmarks in the image, such as the retinal blood vessels, can be utilized to assess the alignment quality with respect to each offset vector selected. Another example of quality index can be a measure of accuracy and smoothness of feature curve(s) such as 910, 920 and 930 in FIG. 9.

FIG. 10 shows an example in which all the alignment offset vectors for each of the 2D OCT images ($\Delta X_i$, $\Delta Y_i$, and $\Delta Z_i$) are set to (0, 0, 0). Here, the reference numeral 'i' denotes a particular 2D OCT scan, whereby the method described herein may include a selected group or all of the 2D OCT scans in the 3D data set, according to some embodiments of the present invention. In FIG. 10, the alignment offset vectors are set to zeros and the SSLO image 1000 is generated as if 3D alignment was not performed. The eye-motion defects 1030 can be observed by reference to the "broken" blood vessels in the SSLO image 1000. The ILM and RPE curves disruption can be observed in 1010 and 1020.

The determination of whether an optimal alignment offset vector set has been achieved is by evaluating some measure of alignment quality, such as landmark positions, feature curve accuracy, and feature curve smoothness, against a set of pre-determined threshold values. These threshold values can be pre-determined empirically based on anatomical physiologies and clinical needs. An optimal alignment is achieved by finding the offset vector ($\Delta X_i$, $\Delta Y_i$, and $\Delta Z_i$) for the $i^{th}$ 2D OCT image such that a total score calculated by comparing some measures of alignment quality from the sequence of all OCT images yields the highest score among all possible offset vectors within the respective search ranges. Image processing techniques such as autocorrelation and Fourier transform can be utilized to calculate the score. High-performance computing techniques, such as the hardware-related Streaming SIMD (Single Instruction Multiple Data) Extension (SSE), can also be used to increase the performance speed.

FIG. 11 shows an example in which the optimal alignment is achieved by finding the best alignment offset vector ($\Delta X_i$, $\Delta Y_i$, and $\Delta Z_i$) for each of the $i^{th}$ OCT images. Motion defects 1030 shown in FIG. 10 are removed in the simulated scanning laser ophthalmoscope (SSLO) image 1130. The ILM and RPE curves in 1100 and 1120 show better positional accuracy and smoother results as compared to 1010 and 1020.

The previous descriptions and figures are exemplary only and do not intend to be limiting. One of ordinary skills in the art may identify other embodiments of the present invention that are obvious variations of the embodiments described above. Those alternative embodiments are also intended to be within the scope of this disclosure. As such, the invention is limited only according to the following claims.

We claim:

1. An imaging device, comprising:
   an optical source;
   an x-y scanner receiving light from the optical source and directing the light onto a sample;
   a detector receiving reflected light from the scanner; and
   a computer receiving a signal from the detector and providing a 3D data set containing voxels with a given voxel resolution of a sample, the computer further executing instructions for
   defining a first column and a second column of voxels within the 3D data set, adjacent to each other and extending along a selected direction of the 3D data set;
   defining a step size along the selected direction in the 3D data set;
   summing the voxels in the first and the second column along the selected direction in the 3D data set, alternating between voxels of the first and the second column for each step size along the selected direction of the 3D data set, to obtain values; and
   composing a 2D image using the values.

2. The device in claim 1, wherein composing the 2D image includes defining the value as a pixel of the 2D image for the first column.

3. The device of claim 1, wherein finding values includes
   finding a first 2D surface embedded in the 3D data set according to physical features;
   displacing the first 2D surface along a third dimension within the 3D data set by a selected distance to create a second 2D surface;
   setting alpha channel values within said two surfaces to create a mask; and
   creating a selected 3D data set by integrating voxels in the 3D data set and said mask.

4. The device of claim 3, wherein composing a 2D image includes creating a third 2D surface image from the selected 3D data set.

5. The device of claim 1, wherein the values are obtained within a region of interest in the 3D data set.

6. The device of claim 1, further comprising a gray scale or color lookup table to provide brightness and contrast adjustment to the 2D image.

7. The device of claim 1, wherein the 2D image includes a representation of a simulated scanning laser ophthalmoscope image.

8. The device of claim 7, wherein the 2D image further includes a selected portion of a retina pigment epithelium region or an inner limiting membrane.

9. The device of claim 1, wherein the voxel resolutions in X, Y, and Z directions include a range from 5 μm to 40 μm, 40 μm to 80 μm, and 1 μm to 5 μm, respectively.

10. The device of claim 1, wherein finding values includes correcting for motion error using alignment offset vectors.

11. A method for enhancing ophthalmology images comprising:
    obtaining a 3D image data set containing voxels with a given voxel resolution of a sample;
    defining a first column and a second column of voxels within the 3D data set, adjacent to each other and extending along a selected direction of the 3D data set;
    defining a step size along the selected direction in the 3D data set;
    summing the voxels in the first and the second column along the selected direction in the 3D data set, alternating between voxels of the first and the second column for each step size along the selected direction of the 3D data set, to obtain the values;
    composing a 2D image using the values; and
    displaying the 2D image.

12. The method of claim 11, wherein composing the 2D image includes defining the value as a pixel of the 2D image for the first column.

13. The method of claim 11, wherein finding values includes
    finding a first 2D surface embedded in the 3D data set according to physical features;
    displacing the first 2D surface along a third dimension within the 3D data set by a selected distance to create second 2D surface;
    setting alpha channel values within said two surfaces to create a mask; and
    creating a selected 3D data set by integrating voxels in the 3D data set and said mask.

14. The method of claim 13, wherein composing a 2D image includes creating a third 2D surface image from the selected 3D data set.

15. The method of claim 11, wherein the values are obtained within a region of interest in the 3D data set.

16. The method of claim 11, further comprising a gray scale or color lookup table to provide brightness and contrast adjustment to the 2D image.

17. The method of claim 11, wherein the 2D image includes a representation of a simulated scanning laser ophthalmoscope image.

18. The method of claim 17, wherein the 2D image further includes a selected portion of a retina pigment epithelium region or an inner limiting membrane.

19. The method as recited in claim 11, wherein the voxel resolutions in X, Y, and Z directions include a range from 5 μm to 40 μm, 40 μm to 80 μm, and 1 μm to 5 μm, respectively.

20. The method as recited in claim 11, wherein finding values includes correcting for motion error using alignment offset vectors.

* * * * *